United States Patent [19]

Okamoto

[11] Patent Number: 5,663,311

[45] Date of Patent: Sep. 2, 1997

[54] POLYSACCHARIDE DERIVATIVE AND SEPARATION AGENT

[75] Inventor: Yoshio Okamoto, Aichi, Japan

[73] Assignee: Daicel Chemical Industries, Ltd., Tokyo, Japan

[21] Appl. No.: 549,026

[22] Filed: Oct. 27, 1995

Related U.S. Application Data

[60] Division of Ser. No. 47,118, Apr. 13, 1993, Pat. No. 5,491, 223, which is a continuation-in-part of Ser. No. 877,178, Jun. 25, 1992, abandoned.

[30] Foreign Application Priority Data

Feb. 28, 1991 [JP] Japan ......................... 3-34049

[51] Int. Cl.$^6$ .................. C08B 3/00; C08B 15/05; C08B 37/00
[52] U.S. Cl. ................ 536/18.7; 536/20; 536/30
[58] Field of Search ................ 536/18.7, 30, 20

[56] References Cited

U.S. PATENT DOCUMENTS 3,988,467  10/1976  Dorhofer et al. .................. 424/274
4,818,394   4/1989  Okamoto et al. .................. 536/64
4,997,935   3/1991  Diamantoglou .................... 536/56
5,198,429   3/1993  Konig ................................ 514/58

FOREIGN PATENT DOCUMENTS 63-156538   6/1987   Japan .

*Primary Examiner*—Jeffrey Mullis
*Attorney, Agent, or Firm*—Flynn, Thiel, Boutell & Tanis, P.C.

[57] ABSTRACT

The present invention provides a novel polysaccharide derivative in which part or the whole of the hydroxyl groups or the amino groups contained in a polysaccharide are displaced by two or more kinds of substituents, and a separating agent and a separating apparatus which comprise the polysaccharide derivative.

The polysaccharide derivative of the present invention is extremely useful as a functional material for optical resolution.

1 Claim, No Drawings

POLYSACCHARIDE DERIVATIVE AND SEPARATION AGENT

This is a division of Ser. No. 08/047,118, filed Apr. 13, 1993, now U.S. Pat. No. 5,491,223 which is a continuation-in-part of U.S. Ser. No. 07/877,178, filed Jun. 25, 1992 (now abandoned).

FIELD OF INDUSTRIAL APPLICATION

The present invention relates to a novel polysaccharide derivative which is extremely useful as, e.g., a functional material for optical resolution, and a separating agent comprising said polysaccharide derivative.

PRIOR ART

It has already been known that various racemic modifications can be optically resolved by liquid chromatography using a column packed with a polysaccharide derivative. For example, it is disclosed in Journal of Liquid Chromatography, 9 (2 & 8), 313 to 340 (1986) Japanese Patent Laid-Open No. 142930/1985 and the corresponding patents EP-A 147804 and U.S. Pat. No. 4,818,394, and Japanese Patent Laid-Open No. 178101/1988 and the corresponding patent EP-A 238044.

The present invention aims at providing a separating agent comprising a novel polysaccharide derivative, which is more excellent in resolving power.

DISCLOSURE OF THE INVENTION

The present inventors have extensively studied to solve the above problem and, as a result, have accomplished the present invention.

Namely, the present invention provides a novel polysaccharide in which part or the whole of the hydroxyl groups or the amino groups contained in a polysaccharide are displaced by two or more kinds of substituents, a separating agent or separating apparatus comprising said polysaccharide derivative, and a process for resolving a racemic modification into optical isomers by the use of said separating agent or separating apparatus.

The present invention will now be described in detail.
<Substituent>

The substituents displacing the hydroxyl groups or the amino groups contained in a polysaccharide according to the present invention are as follows:

(1) substituents for hydroxyl group combinations of any groups selected from among those represented by the formulas:

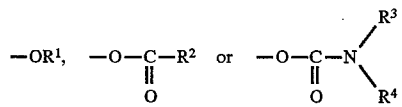

wherein $R^1$ represents an alkyl group such as a methyl, ethyl, propyl, isopropyl, butyl or t-butyl group, a substituted alkyl group wherein the substituent is a halogen or the like, an aromatic group such as a phenyl group, a substituted aromatic group wherein the substituent is an alkyl group having 1 to 8 carbon atoms, a halogen or the like, or an aralkyl group such as a benzyl or phenethyl group; $R^2$, $R^3$ and $R^4$ each represent a hydrogen atom, an alkyl group such as a methyl, ethyl, propyl, isopropyl, butyl or t-butyl group, a substituted alkyl group wherein the substituent is a halogen or the like, an aromatic group such as a phenyl group, a substituted aromatic group wherein the substituent is an alkyl group having 1 to 8 carbon atoms, a halogen atom or the like, or an aralkyl group such as a benzyl or phenethyl group.

(2) substituents for amino group combinations of any groups selected from among those represented by the formula:

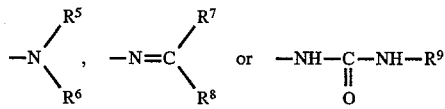

wherein $R^5$ and $R^6$ each represent a hydrogen atom, an alkyl group such as a methyl, ethyl, propyl, isopropyl, butyl or t-butyl group, a substituted alkyl group wherein the substituent is a halogen atom or the like, an aromatic group such as a phenyl group, a substituted aromatic group wherein the substituent is an alkyl group having 1 to 8 carbon atoms, a halogen atom or the like, an aralkyl group such as a benzyl or phenethyl group, or an acyl group such as an acetyl or phenacetyl group, with the proviso that a case wherein $R^5$ and $R^6$ are simultaneously hydrogen atoms is excepted; and $R^7$, $R^8$ and $R^9$ each represent a hydrogen atom, an alkyl group such as a methyl, ethyl, propyl, isopropyl, butyl or t-butyl group, a substituted alkyl group wherein the substituent is a halogen or the like, an aromatic group such as a phenyl group, a substituted aromatic group wherein the substituent is an alkyl group having 1 to 8 carbon atoms, a halogen atom or the like or an aralkyl group such as a benzyl or phenethyl group.

Among the substituents described above, substituents having an aromatic group, particularly, substituents having an aromatic group substituted by an electron-donating group at the 2- and/or 3-position are preferable. The combination of a substituent having an aromatic group substituted by an electron-donating group with a substituent having an aromatic group substituted by an electron-attractive group is particularly preferable. The electron-donating group includes alkyl groups. The combination of a 3,5-dimethylphenylcarbamate group represented by the following formula (i) with a 3,5-dichlorophenylcarbamate group represented by the following formula (II) is still preferable:

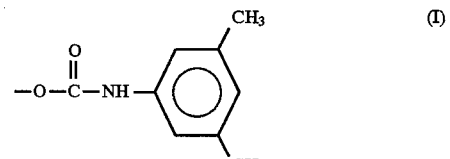

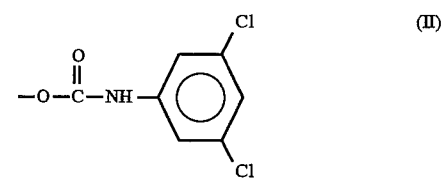

It is preferable that the weight ratio of the 3,5-dimethylphenylcarbamate group (I) to the 3,5-dichlorophenylcarbamate group (II) ranges from 9:1 to 1:9.

The polysaccharide derivative according to the present invention has at least two different substituents. Particularly, a polysaccharide derivative in which the substituents present at the 2- and/or 3-position are different from that present at the 6-position is preferable. The degree of displacement of the polysaccharide derivative according to the present invention is at least 40%, preferably at least 50%, and still preferably at least 85%.

<Polysaccharide>

Although the polysaccharide according to the present invention may be any of synthetic, natural and modified natural ones so far as it is optically active, it is preferably one having a highly ordered bonding mode. Particular examples thereof include α-1,4-glucans (such as amylose and amylopectin), α-1,6-glucans (such as dextran), β-1,4-glucans (such as cellulose), β-1,6-glucans (such as pustulan), β-1,3-glucans (such as curdian and schizophyllan), β-1,3-glucans, β-1,2-glucans (such as crown gall polysaccharide), β-1,4-galactans, β-1,4-mannans, α-1,6-mannans, β-1,2-fructans (such as inulin), β-2,8-fructans (such as levan), β-1,4-xylans, β-1,3-xylans, β-1,4-chitosan, β-1,4-N-acetylchitosan (i.e., chitin), pullulan, agarose, alginic acid and amylose-containing starch, among which amylose, cellulose, β-1,4-chitosan, chitin, β-1,4-mannans, β-1,4-xylans, inulin and curdian are particularly preferable because high-purity polysaccharides can be easily obtained therefrom.

The number-average degree of polymerization of the polysaccharide (the average number of pyranose or furanose rings contained in one polysaccharide molecule) is 5 or above, preferably 10 or above and the upper limit thereof is 2000, preferably 500 from the standpoint of handleability.

<Process for synthesis>

The displacement of the hydroxyl groups or the amino groups of a polysaccharide by the substituents described above can be conducted by the following processes:

(1) Process for displacement of hydroxyl groups

A) displacement to ester

The hydroxyl groups of the polysaccharide according to the present invention can be easily displaced to ester groups by the process in which the corresponding carboxylic acids ($R^2COOH$) are reacted with thionyl chloride or oxalyl chloride to form acid chlorides and then the acid chlorides are reacted with the corresponding polysaccharide in pyridine.

B) displacement to carbamate

The hydroxyl groups of the polysaccharide according to the present invention can be easily displaced to carbamate groups by any conventional process for preparing a urethane from an alcohol and an isocyanate. For example, they can be displaced to carbamate groups by reacting The corresponding isocyanates ($R^3NCO$) with a polysaccharide in a suitable solvent in the presence of a catalyst, e.g., a Lewis base such as a tertiary amine or a Lewis acid such as a tin compound. The isocyanate can be easily prepared by, for example, reacting the amino group of the corresponding aniline derivative with phosgene.

C) displacement to ether

The hydroxyl groups of the polysaccharide according to the present invention can be easily displaced to ether groups by reacting the corresponding halides ($R^1X$ wherein X represents a halogen atom) with the corresponding polysaccharide in a solvent such as dioxane or pyridine in the presence of a base such as potassium hydroxide or potassium t-butoxide.

(2) Process for displacement of amino groups (D) displacement to vinylidene

The amino groups of the polysaccharide according to the present invention can be displaced to vinylidene groups by any conventional process for preparing a Schiff base from an amine and a carbonyl compound.

(E) displacement to amide

The amino groups of the polysaccharide according to the present invention can be displaced to amide groups by any conventional process for preparing an amide from an amine and an acid chloride.

(F) displacement to urea

The amino groups of the polysaccharide according to the present invention can be displaced to urea by any conventional process for preparing urea from an amine and an isocyanate.

According to the present invention, the hydroxyl groups or the amino groups of a polysaccharide must be displaced by at least two kinds of substituents, which can be attained by simultaneously reacting two or more reactants as described above with a polysaccharide or by stepwise reacting them with a polysaccharide to Thereby displace specified hydroxyl group(s) or amino group(s) by specified substituents.

Among the polysaccharide derivatives of the present invention, a polysaccharide derivative having a 3,5-dimethylphenylcarbamate group represented by the above formula (I) and a 3,5-dichlorophenylisocyanate group represented by the above formula (II) can be prepared by reacting a polysaccharide with 3,5-dimethylphenyl isocyanate and 3,5-dichlorophenyl isocyanate. This reaction can be conducted by any conventional process for preparing a urethane from an alcohol and an isocyanate. For example, the above polysaccharide derivative can be prepared by reacting the corresponding isocyanates with a polysaccharide in a suitable solvent in the presence of a Lewis base such as a tertiary amine or a Lewis acid such as a tin compound as a catalyst.

<Separating agent>

The polysaccharide derivative of the present invention is an extremely useful substance as a functional material, particularly as a packing for optical resolution, i.e., a separating agent.

The separation of a mixture of compounds or a mixture of optical isomers by the use of the polysaccharide derivative according to the present invention as a separating agent is generally conducted by a chromatographic process such as gas chromatography, liquid chromatography or thin-layer chromatography. Alternatively, it can be also conducted according to a membrane separation process by the use of a membrane containing the polysaccharide derivative according to the present invention.

When the polysaccharide derivative of the present invention is applied to liquid chromatography as a separating agent, it is favorable from the standpoints of easiness and simplicity that the polysaccharide derivative be packed into a column in powdery form. It is preferable that the polysaccharide derivative of the present invention be pulverized or converted into beads and it is still preferable that the resulting particle be porous. Further, it is desirable that the polysaccharide derivative be supported on a carrier for the purpose of improving the pressure resistance of the separating agent, preventing the separating agent from undergoing swelling or shrinkage due to the replacement of the solvent, and improving the number of theoretical plates.

When the polysaccharide derivative of the present invention is used in powdery form, the sizes of the particle and the carrier are 1 μm to 1 mm, preferably 1 μm to 300 μm, though they vary depending upon the size of the column to be used. It is desirable that the carrier be porous with the mean pore diameter being 10 Å to 100 μm, preferably 50 Å to 50000 Å. The amount of the polysaccharide derivative to be supported on a carrier is 1 to 100% by weight, preferably 5 to 50% by weight based on the carrier.

The polysaccharide derivative may be supported on a carrier by a chemical or physical process. The physical process includes a process of dissolving the polysaccharide derivative in a solvent wherein it is soluble, mixing the obtained solution with a carrier fully and blowing out the solvent with an air stream either under a reduced pressure or under heating and a process of dissolving the polysaccharide derivative in a solvent wherein it is soluble, mixing the obtained solution with a carrier fully and treating the obtained mixture with another solvent in which the polysaccharide derivative is insoluble to diffuse the former solvent in the latter solvent. The separating agent thus prepared may be further subjected to suitable treatment such as heating, addition of a solvent or washing in order to improve the separating power thereof.

The carrier to be used in the present invention may be a porous organic carrier or a porous inorganic carrier, with the use of a porous inorganic carrier being preferable. Suitable examples of the porous organic carrier include polymers such as polystyrene, polyacrylamide and polyacrylate. On the other hand, suitable examples of the porous inorganic carrier include silica, alumina, magnesia, glass, kaolin, titanium oxide and silicates, which may be surface-treated for the purpose of improving the affinity thereof with the polysaccharide derivative and the surface characteristics of the carrier itself. The surface treatment includes a treatment with an organic silane compound and a treatment with plasma polymerization.

When the polysaccharide derivative of the present invention is used in liquid chromatography or thin-layer chromatography, the developer to be used is not particularly limited except for ones which dissolve the polysaccharide derivative or react with it. When the polysaccharide derivative is chemically supported on a carrier or insolubilized by crosslinking, all developers are usable except ones reactive with it.

When the polysaccharide derivative is used in thin layer chromatography, a layer comprising the separating agent in the form of a particle having a size of 0.1 μm to 0.1 mm and, if necessary, a small amount of a binder is formed on a base in a thickness of 0.1 μm to 100 mm.

Further, when the polysaccharide derivative is applied to a membrane separation process, it is used as a hollow yarn or a film.

EXAMPLE

The present invention will now be described in more detail by referring to the following Examples, though the present invention is not limited to them.

Example 1

0.722 g of cellulose (Avicel, a product of Merck), 0.988 g (6.71 mmol, 50% by equivalent) of 3,5-dimethylphenyl isocyanate and 1.243 g (6.68 mmol, 50% by equivalent) of 3,5-dichlorophenyl isocyanate were added To 35 ml of pyridine (which had been simple-distilled and dried over with KOH). The obtained mixture was maintained at about 100° C. for 15 hours to conduct a reaction, followed by the addition thereto of 0.485 g (3.30 mmol) of 3,5-dimethylpheny isocyanate and 0.613 g (3.30 mmol) of 3,5-dichlorophenyl isocyanate. The obtained mixture was stirred at 110° C. for 10 hours and poured into methanol to give precipitates, which were collected on a glass filter, fully washed with methanol, and vacuum-dried at 60° C. for 2 hours. Thus 2.761 g of a cellulose derivative was obtained in a yield of 93.2%. Hereinafter, this cellulose derivative is referred to as "Cellulose derivative (1)".

Example 2

1.01 g of cellulose (Avicel, a product of Merck), 1.85 g (12.45 mmol, 87% by equivalent) of 3,5-dimethylphenyl isocyanate and 1.18 g (6.24 mmol, 33% by equivalent) of 3,5-dichlorophenyl isocyanate were added to 35 ml of pyridine (which had been simple-distilled and dried over with KOH). The obtained mixture was maintained at about 100° C. for 15 hours to conduct a reaction, followed by the addition thereto of 15 ml of pyridine, 0.54 g (3.73 mmol) of 3,5-dimethylphenyl isocyanate and 0.34 g (1.83 mmol) of 3,5-dichlorophenyl isocyanate. The obtained mixture was stirred at 100° C. for 24 hours and poured into methanol to give precipitates, which were collected on a glass filter, fully washed with methanol, and vacuum-dried at 80° C. for 2 hours. Thus 3.520 g of a cellulose derivative was obtained in a yield of 100%. Hereinafter, this cellulose derivative is referred to as "Cellulose derivative (2)".

Example 3

1.68 g of tritylcellolose (degree of substitution by trityl group: 43%) was dissolved in 20 ml of pyridine, followed by the addition thereto of 1.75 g (excess based on the residual hydroxyl group) of 3,5-dimethylphenylisocyanate. The obtained mixture was maintained at about 100° C. for 9 hours to conduct a reaction. The reaction mixture was poured into methanol to give precipitates, which were collected on a glass filter and fully washed with methanol.

1.45 g of the cellulose derivative thus prepared was suspended in 40 ml of methanol, followed by the addition thereto of four drops of concentrated hydrochloric acid. The obtained mixture was stirred at room temperature for 20 hours to remove the trityl groups from the cellulose derivative. The resulting cellulose derivative was collected on a glass filter, washed with methanol and vacuum-dried at 60° C. for 2 hours (weight of product: 0.770 g, yield: 92.3%).

0.77 g of the cellulose derivative prepared above and 1.10 g (5.93 mmol, excess) of 3,5-dichloropheny isocyanate were dissolved in 15 ml of pyridine. The obtained solution was maintained at about 100° C. for 15 hours to conduct a reaction. The reaction mixture was poured into methanol to give precipitates, which were collected by centrifuging, washed with methanol repeatedly, dried in a desiccator for about 3 hours, and vacuum-dried at 60° C. for 2 hours. Thus 1.045 g of cellulose derivative was obtained in a yield of 86.3%.

The obtained cellulose derivative was one selectively modified with a 3,5-dichlorophenyl-carbamate group at the 6-position and 3,8-dimethylphenylcarbamate groups at the 2- and 3-positions, which is hereinafter referred to as "Cellulose derivative (3)".

The results of elemental analysis of the Cellulose derivatives (1) to (3) prepared in the Examples 1 to 3 are given in Table 1. For reference, the results of elemental analysis of cellulose tris(3,5-dichlorophenylcarbamate) (reference 1) and cellulose tris(3,5-dimethylphenylcarbamate) (reference 2) are also given in Table 1.

TABLE 1

| Cellulose derivative | Results of elemental analysis | | | | Content of Cl* (%) |
|---|---|---|---|---|---|
| | C % | H % | N % | Cl % | |
| (1) | 51.01 | 3.79 | 6.10 | 19.46 | 62.19 |
| (2) | 56.09 | 4.72 | 5.89 | 12.42 | 42.39 |
| (3) | 52.71 | 3.81 | 5.88 | 18.73 | 59.57 |
| ref. 1 | 44.66 | 2.64 | 5.79 | 29.30 | — |
| ref. 2 | 65.66 | 6.18 | 6.96 | — | — | note)
*the content of 3,5-dichlorophenylcarbamate group calculated from the Cl content determined by the elemental analysis.

Example 4

0.7 g of each of the Cellulose derivatives (1) to (3) prepared in the Examples 1 to 3 and the reverential ones 1 and 2 was dissolved in 15 ml of tetrahydrofuran. The obtained solutions were each supported on 3.0 g of silica gel (a product of Merck, SI4000) treated with 3-aminopropyltriethoxysilane to give various packings.

These packings were each packed into a column having a length of 25 cm and an inner diameter of 0.46 cm with the use of a hexane/liquid paraffin (2:1) mixture.

Various racemic compounds listed in Tables 2 and 3 were resolved by the use of the columns prepared above. The results are given in Tables 2 and 3.

The capacity ratio (k') and separation factor ($\alpha$) given in the Tables were calculated by the following formulas, respectively:

$$\text{capacity ratio } (k') = \frac{\text{retention time of separated compound} - \text{dead time}}{\text{dead time}}$$

$$\text{separation factor } (\alpha) = \frac{\text{capacity ratio of more strongly adsorbed compound}}{\text{capacity ratio of more weakly adsorbed compound}}$$

TABLE 2

| Racemic modification | Ref. 1 | | Ref. 2 | | Cellulose deriv. (1) | | Cellulose deriv. (2) | | Cellulose deriv. (3) | |
|---|---|---|---|---|---|---|---|---|---|---|
| | k' | α | k' | α | k' | α | k' | α | k' | α |
| 1. (O, C6H5, C6H5) *1 | 0.56(+) | 1.84 | 0.74(−) | 1.68 | 0.36(+) | 2.03 | 0.37(−) | ~1 | 0.35(+) | 1.80 |
| 2. (N...N structure) *1 | 0.87(+) | 1.65 | 0.97(+) | 1.32 | 0.53(+) | 1.84 | 0.46(+) | 1.32 | 0.52(+) | 1.39 |
| 3. Co(acac)₃ *1 | 0.76(+) | 1.82 | 0.42(+) | ~1 | 0.36(+) | 1.69 | 0.28(+) | 1.41 | 0.47(+) | 1.50 |
| 4. (CONHC6H5, CONHC6H5) *1 | 0.59(+) | 1.41 | 0.83(+) | 3.17 | 0.66(+) | ~1 | 0.49(+) | 1.17 | 0.68(−) | 1.20 |
| 5. (O, C6H5 cyclohexanone) *1 | 2.65(−) | 1.26 | 1.17(−) | 1.15 | 1.47(−) | 1.26 | 0.69(−) | 1.22 | 0.97(−) | 1.28 |

TABLE 2-continued

| Racemic modification | | Ref. 1 | | Ref. 2 | | Cellulose deriv. (1) | | Cellulose deriv. (2) | | Cellulose deriv. (3) | |
|---|---|---|---|---|---|---|---|---|---|---|---|
| | | k' | α | k' | α | k' | α | k' | α | k' | α |
| 6. 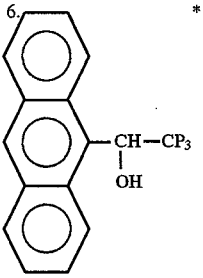 | *1 | 0.28(−) | 1.38 | 2.13(−) | 2.59 | 0.37(−) | 1.50 | 0.45(−) | 1.72 | 0.44(−) | 1.37 |

TABLE 3

| Racemic modification | | Ref. 1 | | Ref. 2 | | Cellulose deriv. (1) | | Cellulose deriv. (2) | | Cellulose deriv. (3) | |
|---|---|---|---|---|---|---|---|---|---|---|---|
| | | k' | α | k' | α | k' | α | k' | α | k' | α |
| 7. 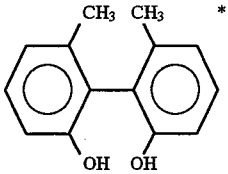 | *1 | 1.62(+) | 1.11 | 2.36(−) | 1.83 | 1.48(−) | 1.36 | 1.01(−) | 1.82 | 1.08(−) | 1.30 |
| 8. 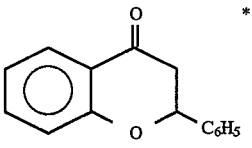 | *1 | 1.55(−) | 1.20 | 1.47(−) | 1.41 | 1.03(−) | 1.20 | 0.63(−) | 1.22 | 0.77(−) | 1.15 |
| 9. C₆H₅—CH—C—C₆H₅ <br> \| \|\| <br> OH O | *1 | 3.08(−) | 1.21 | 2.43(+) | 1.58 | 2.08(−) | 1.07 | 1.37(+) | 1.19 | | |
| 10. (C₆H₅)₃C—CH—OH <br> \| <br> C₆H₅ | *1 | 0.40(+) | 1.29 | 1.37(+) | 1.34 | 0.47(+) | ~1 | 0.48(+) | ~1 | 0.43(+) | 1.14 |
| 11. 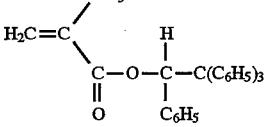 | *2 | 0.48(+) | 4.23 | 0.37(−) | 1.73 | 0.52(+) | 2.77 | 0.72(+) | 1.25 | 0.54(+) | 1.68 | note)
*1 eluent: n-hexane/2-propanol (90:10)
*2 eluent: n-hexane/2-propanol (98:2)

Example 5

Five grams (30.5 mmol) of cellulose (Avicel, tradename of Merck) and 20 g (71.7 mmol) of trityl chloride were reacted with each other in 80 ml of dry pyridine at 80° C. for 24 hours. The product mixture was found to turn clear yellow. It was then poured into 400 ml of methanol to precipitate. 6.20 g of 6-O-tritylcellulose was collected with a glass filter. The production yield was 93.3%. The elementary analysis was 57.73% of C and 8.05% of H, while the calculated values were 55.04% of C and 8.26 of H. 3.0 g (13.8 mmol) of 6-O-tritylcellulose and 5.35 g (36.4 mmol) of 3,5-dimethylphenyl isocyanate were reacted with each other in 20 ml of dry pyridine at 80° C. for about 24 hours. The product solution was then poured into methanol to precipitate. 6.21 g, a production yield of 80.3%, of 6-O-trityl-2,3-bis(3,5-dimethylphenylcarbamate) of cellulose was collected with a glass filter. The elementary analysis was 58.46% of C, 6.98% of H and 4.44% of N, while the calculated values were 59.79% of C, 6.41% of H and 4.98% of N.

2.0 g of 6-O-trityl-2,3-bis(3,5-dimethylphenylcarbamate) of cellulose was stirred in a mixture of 0.5 ml of hydrochloric acid and 100 ml of methanol for about 20 hours. The product mixture was treated centrifugally, decanted and dried. 1.68 g; a production yield of 97%, of 6-hydroxy-2,3-bis(3,5-dimethylphenylcarbamate) of cellulose (5) was obtained, having an elementary analysis of 60.04% of C, 5.21% of H and 5.22% of N, while the calculated values were 59.02% of C, 4.9% of H and 5.74% of N. Hereinafter, this cellulose derivative is referred to as "cellulose (5)".

Example 6

1.02 g (2.23 mmol) of 6-hydroxy-2,3-bis(3,5-dimethylphenylcarbamate) of cellulose (5) was reacted with 0.32 g (4.10 mmol) of acetyl chloride to obtain 1.07 g (96% yield) of 6-acetyl-2,3-bis(3,5-dimethylphenylcarbamate) of cellulose (6), having an elementary analysis of 62.04% of C, 6.21% of H and 5.42% of N, while the calculated values were 62.70% of C, 6.02% of H and 5.62% of N. Hereinafter, this cellulose derivative is referred to as "cellulose (6)".

Example 7

0.80 g (1.80 mmol) of 6-hydroxy-2,3-bis(3,5-dimethylphenylcarbamate) of cellulose (5) was reacted with 0.20 g (3.51 mmol) of methyl isocyanate to obtain 0.90 g (98% yield) of 6-methylcarbamate-2,3-bis(3,5-dimethylphenylcarbamate) of cellulose (7), having an elementary analysis of 60.01% of C, 5.92% of H and 8.46% of N, while the calculated values were 60.82% of C, 6.04% of H and 8.19% of N. Hereinafter, this cellulose derivative is referred to as "cellulose (7)".

Example 8

0.82 g (1.80 mmol) of 6-hydroxy-2,3-bis(3,5-dimethylphenylcarbamate) of cellulose (5) was dissolved in 15 ml of dry dimethylformamide. To the solution were added 5 ml of dry pyridine and 0.53 g (3.77 mmol) of benzoyl chloride. The mixture was stirred at 80° C. for 24 hours. 0.98 g (97.2% yield) of 6-benzoate-2,3-bis(3,5-dimethylphenylcarbamate) of cellulose (8) was obtained, having an elementary analysis of 66.57% of C, 5.92% of H and 5.10% of N, while the calculated values were 66.40% of C, 5.71% of H and 5.00% of N. Hereinafter, this cellulose derivative is referred to as "cellulose (8)".

Example 9

0.90 g (1.97 mmol) of 6-hydroxy-2,3-bis(3,5-dimethylphenylcarbamate) of cellulose (5) was reacted with 0.46 g (3.84 mmol) of phenyl isocyanate in 15 ml dry pyridine to obtain 1.11 g (98% yield) of 6-phenylcarbamate-2,3-bis(3,5-dimethyphenylcarbamate) of cellulose (9), having an elementary analysis of 64.90% of C, 5.30% of H and 7.52% of N, while the calculated values were 64.69% of C, 5.78% of H and 7.33% of N. Hereinafter, this cellulose derivative is referred to as "cellulose (9)".

Example 10

0.91 g (2.00 mmol) of 6-hydroxy-2,3-bis(3,5-dimethylphenylcarbamate) of cellulose (5) was dissolved in 15 ml of dry dimethylformamide. To the solution were added 5 ml of dry pyridine and 0.52 g (3.09 mmol) of 3,5-dimethylbenzoyl chloride. The mixture was stirred at 80° C. for 24 hours. 1.04 g (88.5% yield) of 6-(3,5-dimethylbenzoate)-2,3-bis(3,5-dimethylphenylcarbamate) of cellulose (10) was obtained, having an elementary analysis of 67.57% of C, 6.17% of H and 4.89% of N, while the calculated values were 67.30% of C, 6.12% of H and 4.76% of N. Hereinafter, this cellulose derivative is referred to as "cellulose (10)".

Example 11

0.75 g of each of the Cellulose derivatives (5) to (10) prepared in the Examples 5 to 10 was dissolved in 15 ml of tetrahydrofuran. The obtained solutions were each supported on 3.0 g of silica gel (a product of Merck, SI4000) treated with 3-aminopropyltriethoxysilane to give various packings.

These packings were each packed into a column having a length of 25 cm and an inner diameter of 0.46 cm with the use of a hexane/liquid paraffin (2:1) mixture.

Various racemic compounds listed in Tables 2, 3 and 4 were resolved by the use of the columns prepared above. The results are given in Table 4.

TABLE 4

Separation factors (α) in the optical resolution of cellulose derivatives 4a–4f

| Type | Polysaccharide derivatives Formula 2,3- | 6- | Racemic modification No. 7 | 1 | 2 | 4 | 3 |
|---|---|---|---|---|---|---|---|
| Cellulose (5) | Me$_2$C$_6$H$_3$NHCO | H | 2.08(−) | ~1(+) | 1.42(+) | 1.31(+) | ~1(+) |
| Cellulose (6) | Me$_2$C$_6$H$_3$NHCO | MeCO | 1.90(−) | ~1(+) | 1.18(−) | ~1(−) | 1.15(−) |
| Cellulose (7) | Me$_2$C$_6$H$_3$NHCO | MeNHCO | 2.19(−) | ~1(+) | 1.75(+) | 1.23(−) | 1.00 |
| Cellulose (8) | Me$_2$C$_6$H$_3$NHCO | C$_6$H$_5$CO | 2.10(−) | 1.25(+) | 1.56(+) | 1.19(+) | ~1(+) |
| Cellulose (9) | Me$_2$C$_6$H$_3$NHCO | C$_6$H$_5$NHCO | 2.30(−) | ~1(+) | 1.45(+) | 1.16(+) | 1.38(+) |
| Cellulose (10) | Me$_2$C$_6$H$_3$NHCO | Me$_2$C$_6$H$_3$CO | 2.06(−) | 1.27(+) | 1.76(+) | 1.26(−) | ~1(+) |

The embodiments of the invention in which an exclusive property or privilege is claimed are defined as follows:

1. A polysaccharide derivative in which the substituents present at the 2- and/or 3-position are different from that present at the 6-position comprising a polysaccharide having some or all of the hydroxyl or amino groups contained therein substituted by two or more kinds of substituents, one of the substituents being a 3,5-dimethylphenylcarbamate group at the 2- and/or 3-position of the polysaccharide and another of the substituents being a member selected from the group consisting of 6-MecO, 6-MeNHCO, 6-C$_6$H$_5$CO, 6-C$_6$H$_5$NHCO and 6-Me$_2$C$_6$H$_3$CO.

* * * * *

UNITED STATES PATENT AND TRADEMARK OFFICE
CERTIFICATE OF CORRECTION

PATENT NO. : 5,663,311
DATED : September 2, 1997
INVENTOR(S) : Yoshio OKAMOTO

It is certified that error appears in the above-indentified patent and that said Letters Patent is hereby corrected as shown below:

Column 12, line 64; change "6-MecO" to ---6-MeCO---.

Signed and Sealed this

Seventeenth Day of February, 1998

Attest:

BRUCE LEHMAN

Attesting Officer     Commissioner of Patents and Trademarks